(12) United States Patent
Petrucelli

(10) Patent No.: US 7,809,436 B2
(45) Date of Patent: Oct. 5, 2010

(54) TWO WIRE OSCILLATOR SYSTEM FOR DETERMINING BODY IMPEDANCE

(75) Inventor: Steven Petrucelli, Cranbury, NJ (US)

(73) Assignee: Measurement Ltd., Grand Cayman (KY)

(*) Notice: Subject to any disclaimer, the term of this patent is extended or adjusted under 35 U.S.C. 154(b) by 659 days.

(21) Appl. No.: 11/286,955

(22) Filed: Nov. 23, 2005

(65) Prior Publication Data

US 2006/0111645 A1 May 25, 2006

Related U.S. Application Data

(60) Provisional application No. 60/631,042, filed on Nov. 24, 2004.

(51) Int. Cl.
*A61B 5/05* (2006.01)
(52) U.S. Cl. ..................... 600/547; 600/554
(58) Field of Classification Search .................. 600/547
See application file for complete search history.

(56) References Cited

U.S. PATENT DOCUMENTS

| | | | |
|---|---|---|---|
| 3,601,714 A | 8/1971 | Vespie et al. | |
| 3,694,804 A | 9/1972 | Hill | |
| 4,646,754 A | 3/1987 | Seale | |
| 4,780,661 A | 10/1988 | Bolomey et al. | |
| 4,831,527 A | 5/1989 | Clark | |
| 5,003,267 A * | 3/1991 | Coleman | 324/442 |
| 5,335,667 A | 8/1994 | Cha et al. | |
| 6,295,468 B1 * | 9/2001 | Hess | 600/547 |
| 6,709,380 B2 | 3/2004 | Green et al. | |
| 6,778,030 B2 * | 8/2004 | Kobayashi et al. | 331/73 |
| 7,043,296 B1 | 5/2006 | Kasai et al. | |
| 2001/0051769 A1 | 12/2001 | Hoek et al. | |
| 2003/0016090 A1 * | 1/2003 | Kobayashi et al. | 331/158 |
| 2004/0196054 A9 * | 10/2004 | Liu et al. | 324/692 |

FOREIGN PATENT DOCUMENTS

WO WO 01/37729 5/2001
WO WO 0137729 A1 * 5/2001

OTHER PUBLICATIONS

Horowitz, Paul; Hill, Winfield: "The art of electronics, second edition" 1989, Cambridge University Press, Cambridge, GB, XP002570087 *figure 5.29*.
European Search Report dated Mar. 5, 2010 for counterpart application EP 05 84 7978.
International Search Report dated Jan. 23, 2007 for related PCT Application No. PCT/US05/42663.

* cited by examiner

*Primary Examiner*—Max Hindenburg
*Assistant Examiner*—Michael C Stout
(74) *Attorney, Agent, or Firm*—Howard IP Law Group, PC

(57) ABSTRACT

An apparatus for determining body impedance comprising: first and second electrodes suitable for being electrically coupled to the body; and a variable frequency relaxation oscillator coupled to the electrodes; wherein, the period of oscillation is indicative of the body impedance.

12 Claims, 8 Drawing Sheets

TWO WIRE OSCILLATOR SYSTEM FOR DETERMINING BODY IMPEDANCE

RELATED APPLICATION

This application claims priority of U.S. Patent Application Ser. No. 60/631,042, filed Nov. 24, 2004, the entire disclosure of which is hereby incorporated by reference as if being set forth in its entirety herein.

FIELD OF THE INVENTION

The present invention relates to body impedance measurement devices and techniques.

BACKGROUND OF THE INVENTION

One useful indicator of a person's health is percentage of body fat. One technique for measuring a person's percent body fat is the so-called "bioelectrical impedance" technique. According to this technique, a person's body fat is measured by determining the impedance of the person's body in response to electrical signals. The percent body fat is calculated according to a given formula based upon the measured impedance and other variables such as height, weight, age and sex, for example. Body impedance is typically determined by supplying a constant current through at least two electrodes that contact the body, thereby causing a voltage to develop across the body. This voltage is measured either (1) via the same electrodes through which current is supplied, or (2) via one or more pairs of voltage-measuring electrodes. The body impedance is then calculated from the current and the measured voltage, and the percent body fat may, in-turn, be calculated from the body impedance.

A two wire system has one pair of electrodes that are used for both excitation and sensing. A four wire system has separate pairs of electrodes for excitation and sensing, essentially decoupling the excitation from the response. In the case of a four wire system, current is driven into the body through a pair of excitation electrodes, and sensed independently through a second, independent pair of electrodes. A four wire system typically uses sinusoidal drive waveforms which have no average value, or DC offset, and operates in a sinusoidal steady state such that the resulting potential measured is a sinusoid, as is the magnitude and phase angle relative to the excitation.

By way of further, non-limiting example, at a frequency of 50 Kilohertz (50 Khz), the body impedance is approximately real, since the phase angle is close to zero degrees and the reactive component is extremely small and essentially negligible. The utilization of a four wire system also negates the effects of contact potential changes at the body (e.g., skin)/electrode interface. The electrode is actually operable as a sensor, as it converts electron current in the wire to ionic current in the body. At the interface, a standard cell potential is developed similar to what one would find in an electrochemical cell, such as a battery. The body impedance at 50 KHz, less than 1 milliamp (1 mA) current, is typically less than 1000 ohms ($\Omega$) with a small reactive term. Essentially the impedance under these conditions is real with a negligible reactive term, and hence has a small phase angle (arctangent IM/RE where IM is the Imaginary part and RE is the Real part of the signal component values).

In contrast, conventional two wire systems operate as transient systems having a pulse-recovery response. In such a configuration, a capacitor charges through the body. The current level is low as the body under these conditions represents higher impedance. In some cases the body is not purely resistive and instead can be represented as a series resistor/capacitor network. Typically, the resistive component of the body at these levels and under pulse transient conditions is on the order of hundreds of thousands of ohms (100's of k$\Omega$), and the model is not purely resistive. There is a charge and discharge recovery transient and associated system time constant. The net-effect from a circuit standpoint is a time constant with an impedance of about two orders of magnitude higher than a corresponding four wire system.

Repeatability of measurements in two wire systems can prove problematic. For example, people having thick skin at the body/electrode interface (e.g., calloused feet) may have their impedance measurements skewed since the electrode-skin interface and associated contact potential is not cancelled, as it is in a four wire measurement system. The resistance variations of the electrodes are irrelevant in a four wire Kelvin Bridge measurement system. However, in a two wire measurement system, such variations have a tangible effect, both in capacitance and resistance.

The Body Fat Equation (BFE) for a four wire system has a different weighted coefficient for the impedance term than that for a two wire system, since the impedance measurements have values that are greatly lower than in the two wire case. The sensitivity and span of the impedance measurement for the four wire approach is much less than that of a two-wire system as well.

Accordingly, an alternative two wire approach and circuit for measuring body impedance utilizing a two wire system is believed to be desired.

SUMMARY OF THE INVENTION

An apparatus for determining body impedance comprising: first and second electrodes suitable for being electrically coupled to the body; and a variable frequency relaxation oscillator coupled to the electrodes; wherein, the period of oscillation is indicative of the body impedance.

BRIEF DESCRIPTION OF THE DRAWINGS

Understanding of the present invention will be facilitated by consideration of the following detailed description of the preferred embodiments of the present invention taken in conjunction with the accompanying drawings, in which like numerals refer to like parts, and.

DETAILED DESCRIPTION OF THE PREFERRED EMBODIMENTS

It is to be understood that the figures and descriptions of the present invention have been simplified to illustrate elements that are relevant for a clear understanding, while eliminating, for the purpose of clarity, many other elements found in typical body impedance measurement systems and methods of making and using the same. Those of ordinary skill in the art may recognize that other elements and/or steps may be desirable in implementing the present invention. However, because such elements and steps are well known in the art, and because they do not facilitate a better understanding of the present invention, a discussion of such elements and steps is not provided herein.

According to an aspect of the invention, a two wire or two electrode system uses a variable frequency relaxation oscillator to estimate the impedance of a subject's body. In such a configuration, the period of oscillation may be considered proportional to the bio-impedance, which may optionally be used to calculate body fat related parameters. The oscillator is based upon an Operational Amplifier (OpAmp) with both positive and negative feedback network portions. The subject's body (sometimes simply referred to as the body) is electrically coupled between the OpAmp output and inverting input, thereby providing the negative feedback. The oscillator has a fixed capacitor connected between common (e.g., ground) and the OpAmp inverting input terminal, which is also connected to the variable (body) resistor. This capacitor charges and discharges exponentially through the body with respect to the reference voltage at the OpAmp non-inverting input terminal.

Figure 1:
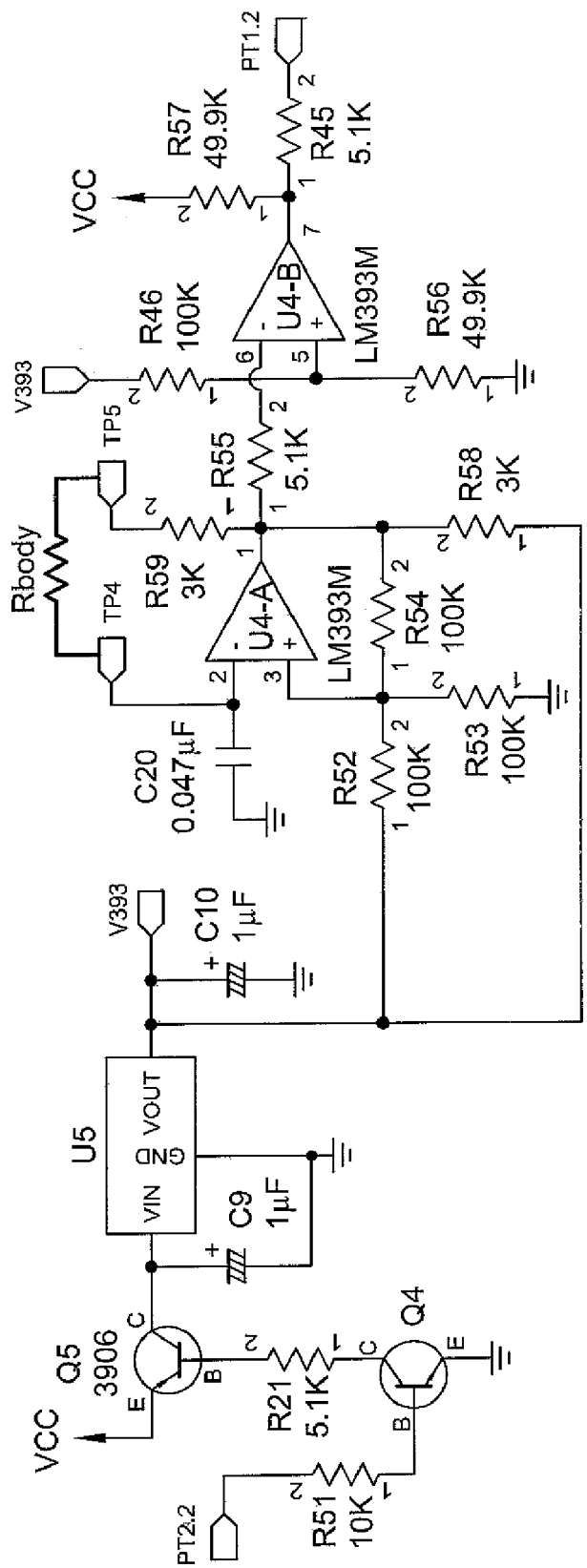
FIGS. 1, 2A-2C illustrate schematic diagrams of a two wire or two electrode oscillator circuit and system employing the oscillator circuit for determining body impedance according to an embodiment of the present invention, respectively.

Referring now to FIG. 1, there is shown an oscillator circuit 100 according to an aspect of the present invention. Circuit 100 is well suited, for use in combination with circuit 200 of FIGS. 2A-2C, for example, for measuring body resistance or impedance according to an aspect of the present invention. Circuit 100 provides for a two electrode or two wire system based upon a variable frequency relaxation oscillator, whose frequency may be used to estimate the impedance of the body. Circuit 200 may be used to integrate circuit 100 into a body scale.

Referring still to FIG. 1, circuit 100 generally includes operational-amplifiers (op-amps) U4-A, U4-B. In the illustrated case, op-amps U4-A, U4-B are each provided in the form of a dual comparator integrated circuit (IC) model LM393M, which is commercially available from National Semiconductor Corporation. A 5.1 kΩ resistor R55 is connected between the output of op-amp U4-A and the inverting input of op-amp U4-B.

Op-amp U4-A is provided with both positive and negative feedback. The body is placed between the output and inverting input terminals of op-amp U4-A, thereby providing negative feedback. More particularly, in the illustrated case the body is coupled to the output of op-amp U4-A via terminal TP5. The body is also coupled through a 0.047 μF fixed capacitor C20 to common, and directly (e.g. shorted) to the inverting terminal of op-amp U4-A via terminal TP4. Thus, capacitor C20 charges and discharges exponentially through the body with respect to the reference voltage at the OpAmp U4-A non-inverting input terminal.

Positive feedback is provided by a fixed 100 kΩ feedback resistor R54, coupled between the output and non-inverting input terminals of op-amp U4-A. The non-inverting input is also coupled to common through a reference 100 kΩ resistor R53. The ratio of the positive feedback resistor R54 to resistor R53 sets the reference voltage for capacitor C20.

More particularly, the output of op-amp U4-A toggles between +/−V saturation. The ratio of resistors R54/R53 sets the voltage at the non-inverting terminal at +/−V saturation/ (N+1). Thus, this parameter controls the threshold for capacitor C20 charging as the period of oscillation is proportional to the time when the capacitor voltage is equal to the threshold voltage.

Circuit 100 further includes a voltage regulator U5. Regulator U5 serves to regulate battery droop caused by circuit 100 operation, such as capacitor C20 charging/discharging. Regulator U5 may take the form of a model #XC61C which is commercially available from Torex Semiconductor for example. An output terminal of regulator U5 is coupled to the non-inverting input terminal of op-amp U4 through a 100 kΩ resistor R52, the output terminal of op-amp U4 through a 3 kΩ resistor R58, and to ground through a 1 μF capacitor C10. The ground terminal of regulator U5 is coupled to ground. The input terminal of regulator U5 is coupled to ground through a 1 μF capacitor C9.

The input terminal of regulator U5 is also coupled to the collector terminal of a transistor Q5. Transistor Q5 may take the form a general purpose, small-signal, PNP transistor, such as model no. 2N3906, which is commercially available from National Semiconductor. The emitter terminal of transistor U5 is coupled to a voltage source Vcc, which may be on the order of about 3 VDC. Voltage source Vcc may take the form of one or more lithium ion batteries, for example. The base terminal of transistor Q5 is coupled through a 5.1 kΩ resistor R2 to a collector terminal of a transistor Q4. Transistor Q4 may take the form a general purpose, small-signal, transistor, such as model no. 2N3904, which is commercially available from Motorola. The emitter terminal of transistor Q4 is coupled to ground, while the base terminal of transistor Q4 is coupled to an output terminal PT2.2 through a 10 kΩ resistor R51.

The output terminal of regulator U5 is also coupled to the non-inverting input terminal of op-amp U4-B through a 100 kΩ resistor R46. The non-inverting input terminal of op-amp U4-B is further coupled to ground through 49.9 kΩ resistor R56. The output of op-amp U4-B is coupled to the supply voltage Vcc through a 49.9 kΩ resistor R57, and to an output terminal PT1.2 through a 5.1 kΩ resistor R45.

It is desirable that oscillator circuit 100 function even in the case of an open or short condition across for the body resistance (e.g., across terminals TP4, TP5). According to an aspect of the present invention, circuit 100 is configured such that the oscillator circuit will oscillate even if a short circuit is placed across the body or the body is insulated from the electrical connections, thereby creating an equivalent open circuit across terminals TP4, TP5. This is accomplished by placing a fixed resistor Rbody across the negative feedback loop, e.g., across terminals TP5, TP4; and a fixed resistor R59 in series with the body. In the illustrated case, resistor R59 is a 3 kΩ resistor. Rbody provides a relatively large resistance, such as a resistance around about several hundred kΩ or greater. As should be understood, it may be important for the system to detect an open or short circuit condition in order to prevent errors in optional body fat calculation. This approach also provides an effective means for system calibration at the time of manufacture by measuring the period of oscillation in the short and open circuit conditions and writing the data into memory, such as a EEPROM.

Figure 3:
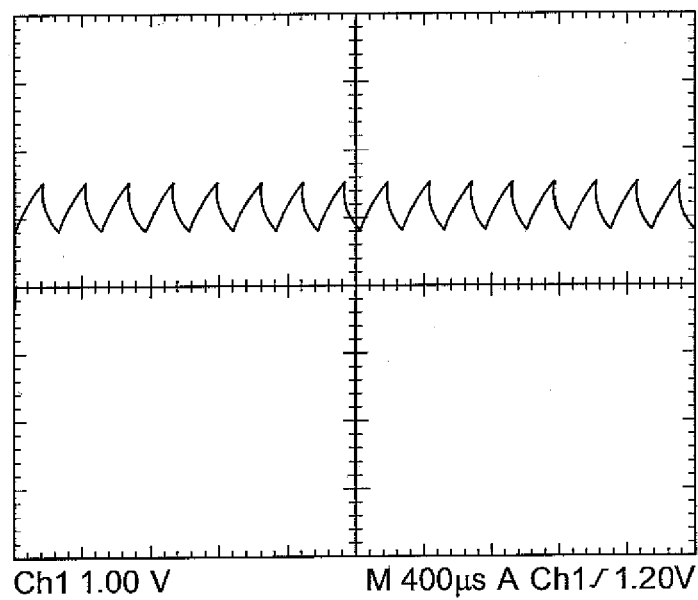
FIGS. 3-5 illustrate exemplary waveforms associated with the left electrode, right electrode, and between electrodes, respectively, for the oscillator circuit and system of the present invention.
Figure 4:
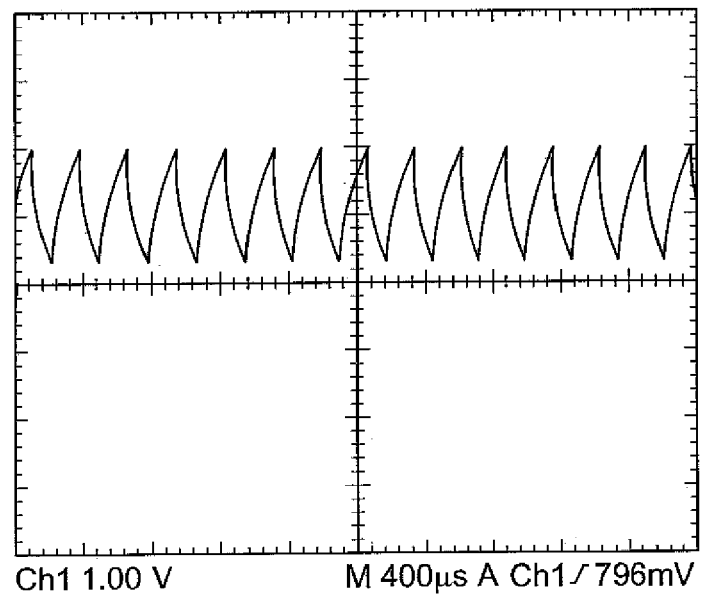
Figure 5:
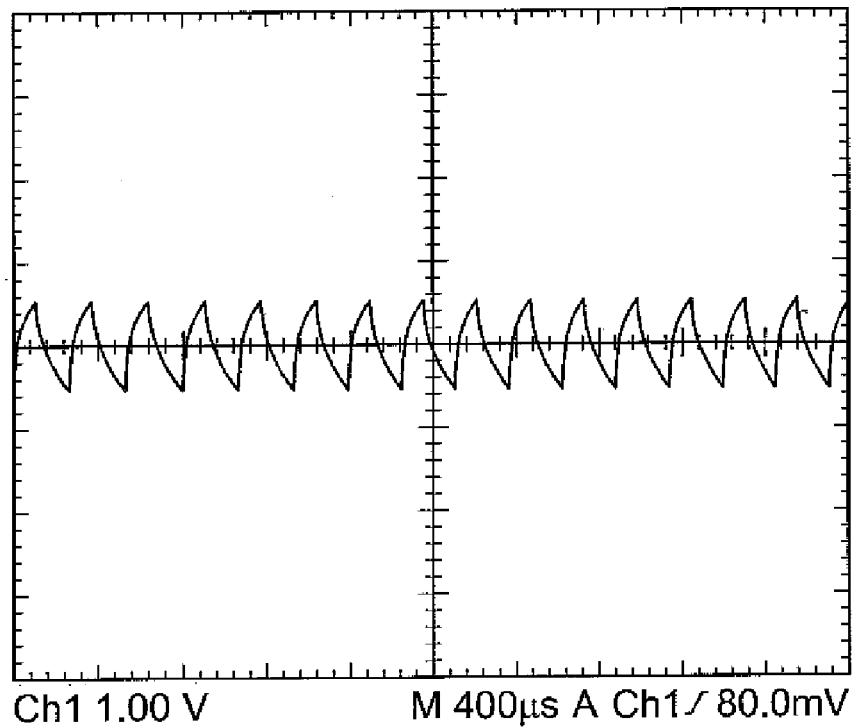

FIG. 3 illustrates an exemplary waveform associated with a first (left) electrode of the present invention (e.g., TP 4) in operation, while FIG. 4 illustrates a waveform for the second (right) electrode (e.g., TP 5) in operation. FIG. 5 shows the waveform between electrodes (e.g., TP4 and TP5) in operation.

Figure 2A:
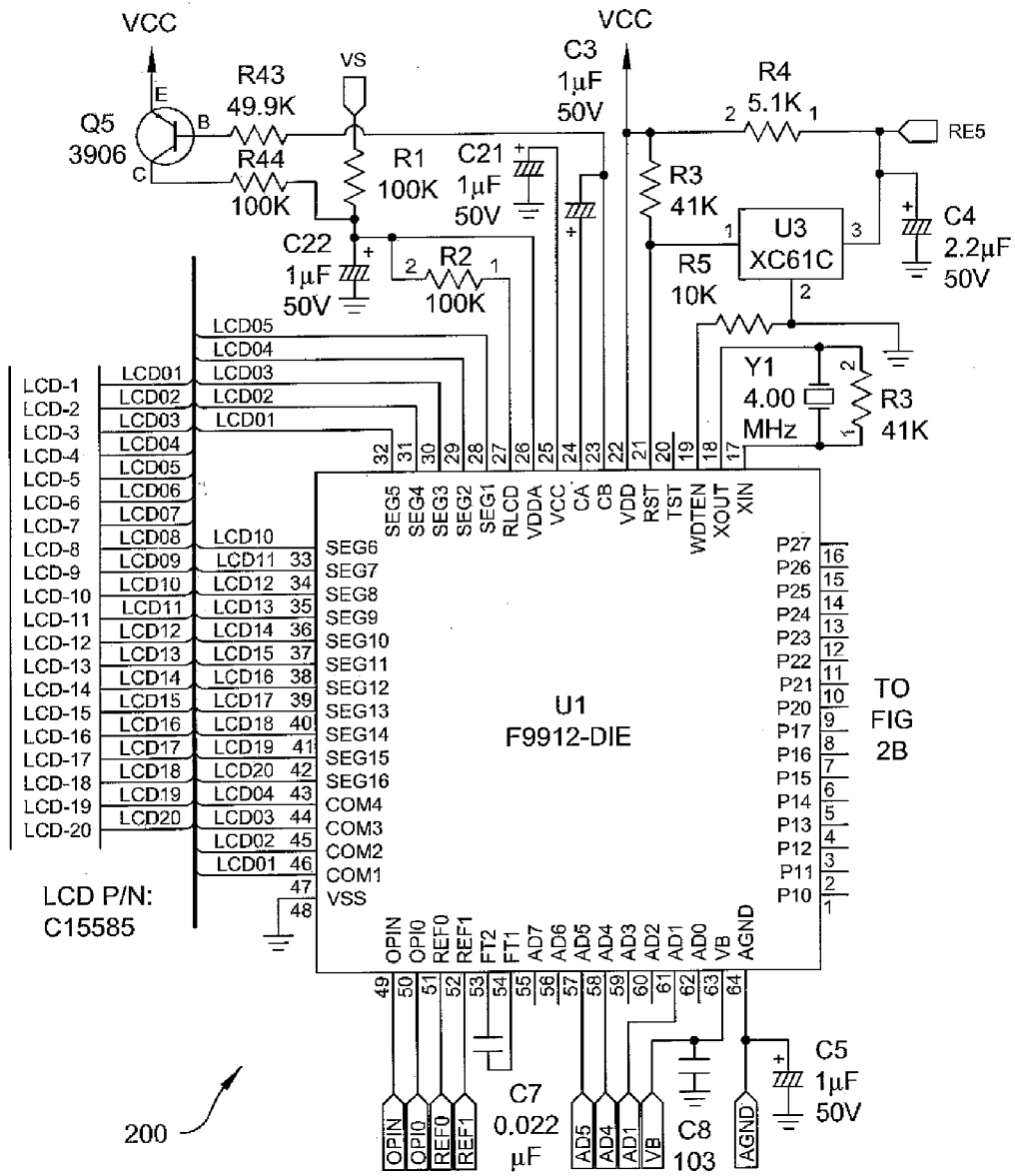
Figure 2B:
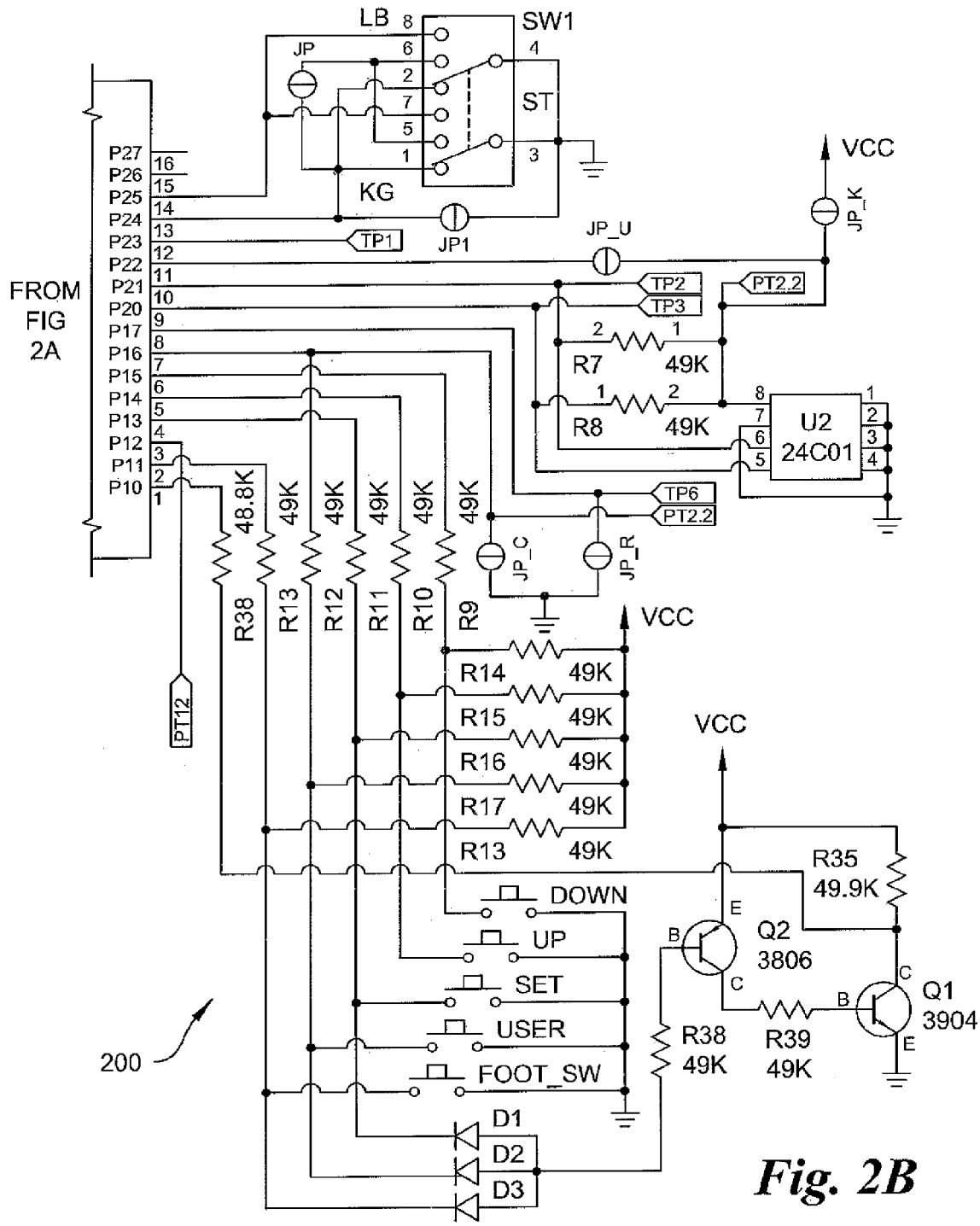
Figure 2C:
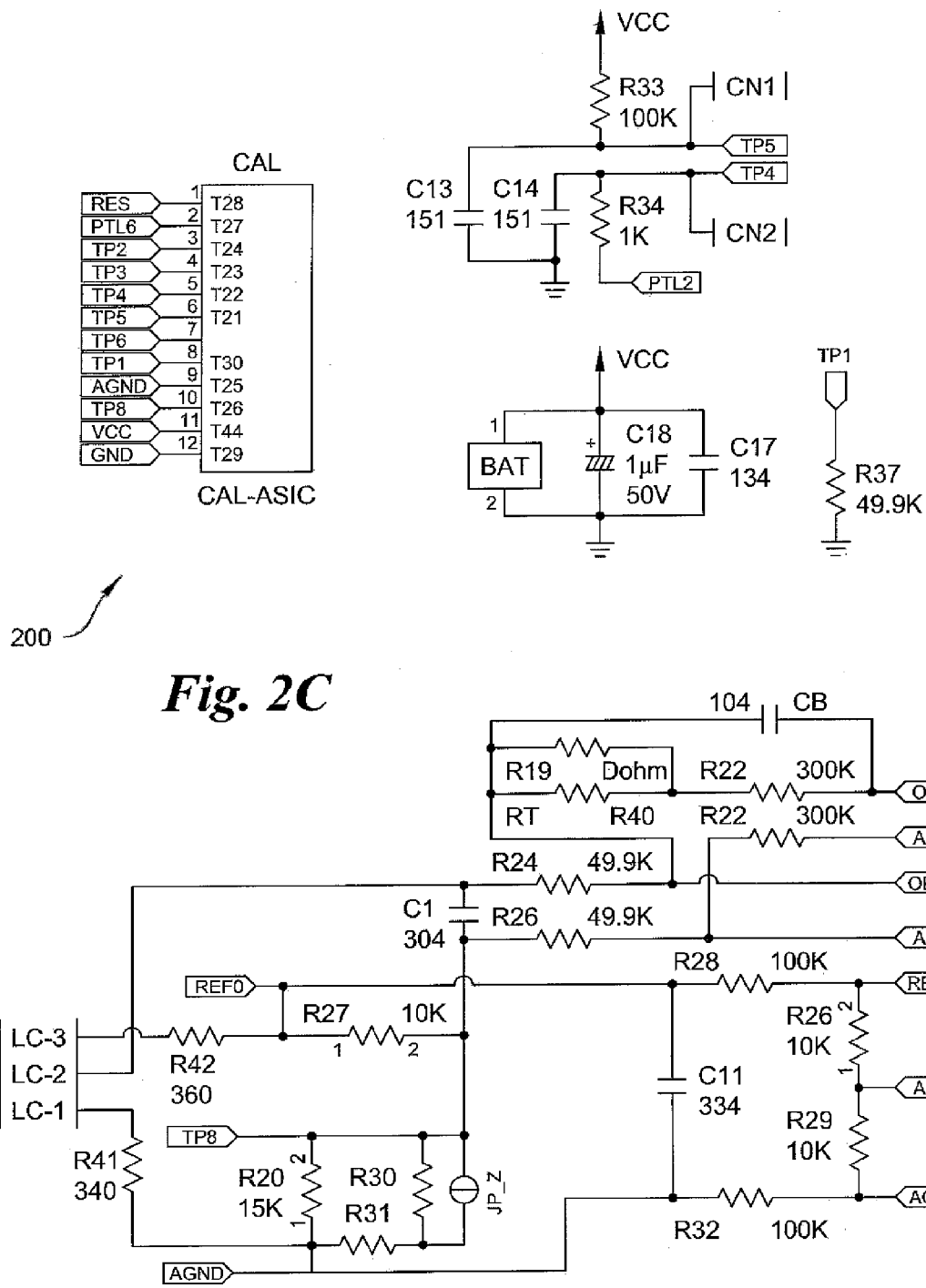

Referring now to FIGS. 2A-2C, circuit 200 is suitable for interfacing with circuit 100 (via outputs PT1.2 and PT2.2), and incorporating circuit 100 into an electronic weighing scale apparatus. Circuit 200 generally includes a microprocessor U1. "Microprocessor", as used herein, refers generally to a computing device including a Central Processing Unit (CPU). A CPU generally includes an arithmetic logic unit (ALU), which performs arithmetic and logical operations, and a control unit, which extracts instructions (e.g., code) from memory and decodes and executes them, calling on the ALU when necessary. "Memory", as used herein, refers to one or more devices capable of storing data, such as in the form of chips, tapes or disks. Memory may take the form of one or more random-access memory (RAM), read-only memory (ROM), programmable read-only memory (PROM), erasable programmable read-only memory (EPROM), or electrically erasable programmable read-only memory (EEPROM) chips, by way of further non-limiting example only. The memory utilized by the processor may be internal or external to an integrated unit including the processor. For example, in the case of a microprocessor, the memory may be internal or external to the microprocessor itself. Circuit 200 includes a memory U2. In the illustrated case, microprocessor U1 takes the form of a general purpose microprocessor model #FS9912, which is commercially available from Fortune Semiconductor, Taiwan. And, memory U2 takes the form of a serial EEPROM memory model 24C01, which is commercially available from MicroChip Corporation. Microprocessor U1 may perform process 700 using memory U2.

Circuit 200 further includes a display, that in the illustrated case is a multi-segment liquid crystal display (LCD) (e.g., LCD-1-LCD-12), user interface buttons/switches (DOWN, UP, SET, USER, FOOT_SW) and other elements found in conventional electronic weighing scale apparatus, such as that described in U.S. Pat. No. 6,292,690, the entire disclosure of which is hereby incorporated by reference herein.

By way of non-limiting further explanation, oscillator circuit 100 and circuit 200 may be placed within the housing of an electronic body weighing scale. The electronic body weighing scale typically further includes a platform for receiving a weight to be measured, supports positioned beneath the platform, and a display assembly. Each support may contain a piezoresistive sensor element or load cell (not shown) that changes an electrical parameter (e.g. resistance) in response to a weight applied to the platform. Conductors operate to couple each of the sensors to the display assembly (e.g., LCD). The display assembly is attached to the platform so as to provide a convenient interface for user input and for display purposes.

The display assembly may be located at the top front portion of the scale platform and includes a display portion such as an LCD display, for example, for viewing the results of a measurement. The assembly further includes an interface portion for entering user input data. In one configuration, the interface portion includes push buttons (e.g., UP/DOWN, SET, USER) sized sufficient to enable input via a user's extremity (e.g. hand or foot). The platform may be formed of an insulating material, and include the pair of electrodes (e.g., TP4, TP5) for a subject's heels or other body parts for both sensing and stimulating. Such a measuring apparatus may include a body impedance/body fat activation switch (UP/DOWN) and user selection switch (e.g., USER) located on a portion of the scale platform for activating the body impedance and body fat determination process (e.g., causing microprocessor U1 to calculate body fat related parameters). Depressing UP/DOWN switch to either a first position (1) or second position (2) activates the body impedance circuitry and causes microprocessor U1 to retrieve data such as characteristics of the particular user associated with the selected USER switch position.

Figure 7:
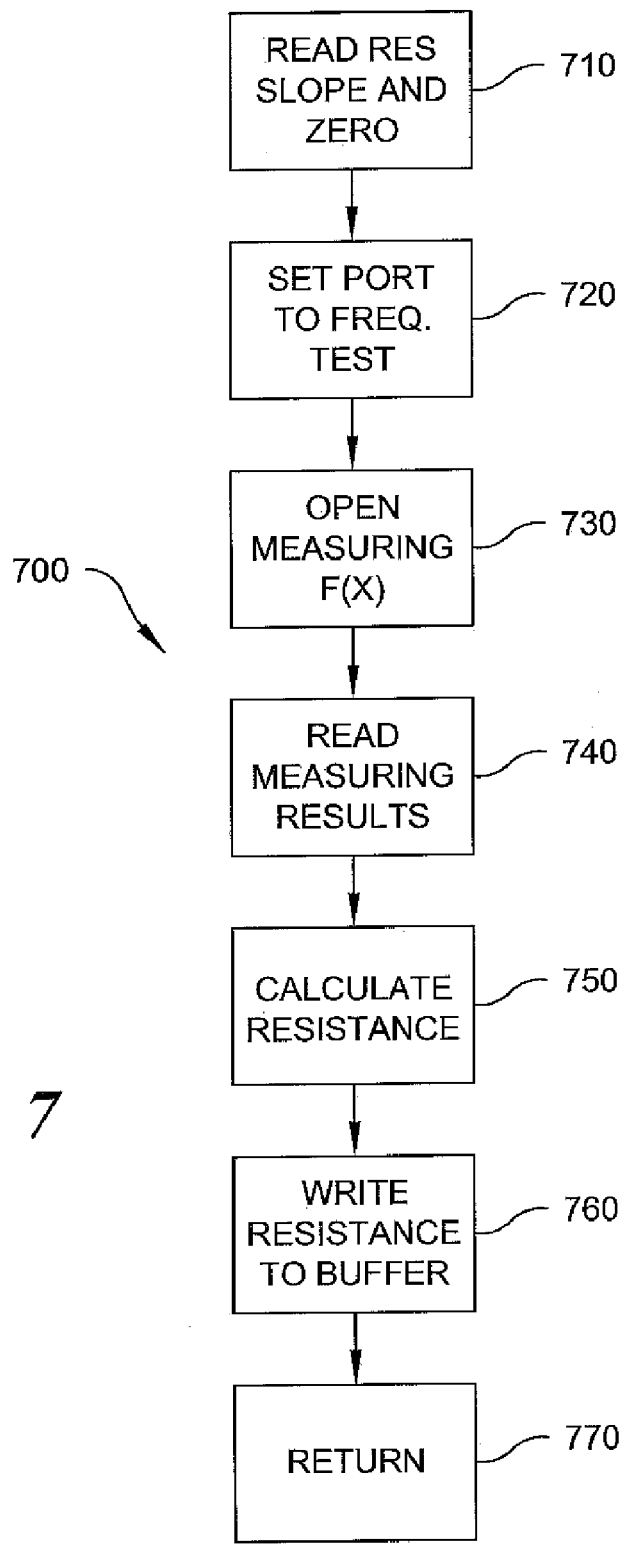
FIG. 7 is a process flow depicting impedance measuring associated with the circuit and system according to an embodiment of the present invention.

Referring now to FIG. 7, there is shown a process flow 700 for measuring a resistance using the circuits of FIG. 1 and FIGS. 2A-2C. Process flow 700 is also useful for determining calibration information using open and short-circuit conditions between electrodes TP4, TP5. Process 700 is suitable for operation by microprocessor U1 and memory U2.

Process flow 700 begins with reading resistance slope (e.g., a span calibration value or coefficient) and a zero value or coefficient from memory (process 710), such as memory U2 associated with microprocessor U1. As will be understood by those possessing an ordinary skill in the pertinent arts, these values correspond to conventional span and zero calibration values. Output terminal (or port) PT1.2 is then designated as receiving input or test frequencies (process 720). A conventional frequency measuring function is then initiated to process signals received on port PT1.2 (process 730). Results of the conventional frequency measuring function are then read or determined (process 740). A body impendence (e.g., resistance) value is then determined (process 750) using the relation: res=(freq$_{zero}$-freq$_{test}$)*slope, where res is the resistance value, freq$_{zero}$ is the determined frequency at the open condition, freq$_{test}$ is the determined frequency at the test condition, and slope is the span coefficient. Finally, the measured resistance value may be stored (process 760) for further use. The span coefficient may be determined using conventional test methodologies, such as by applying known resistances to tune outputs corresponding to measured frequencies.

According to an aspect of the present invention, an index of body fat mass, fat mass index, lean mass index (LMI), and/or body mass index (BMI) may optionally be calculated using entered body data and measured bioelectric impedance. The results, and/or relationships between the BMI and the FMI and/or between the BMI and the LMI may be displayed by way of a graph and/or illustration, for example.

As is well known, body impedance analysis (BIA) may be used to estimate body composition based upon the volume conductor theory—which suggests that the volume of a conductor can be determined by its impedance to current flow. The impedance of a conductor is proportional to its length and is inversely proportional to its cross-sectional area. Thus, the impedance Z of a conductor may be characterized by the equation $$Z = w\left(\frac{L}{A}\right),$$

where w is specific impedance, L is conductor length, and A is cross-sectional area of the conductor. Similarly, the volume V of a conductor can be calculated by measuring the length and the specific impedance of the conductor $$\left(V = w\left(\frac{L^2}{Z}\right)\right).$$

Lean Body Mass (LBM), defined as total body mass less fat body mass, may be estimated since it is known that LBM is a function of total body weight. Once LBM is known, the percentage of body fat (% BF or BF %) can be determined according to the equation $$\%BF = 100\frac{(Wt - LBM)}{Wt},$$

where % BF is percent body fat, LBM is lean body mass, and Wt is total body weight.

Figure 6:
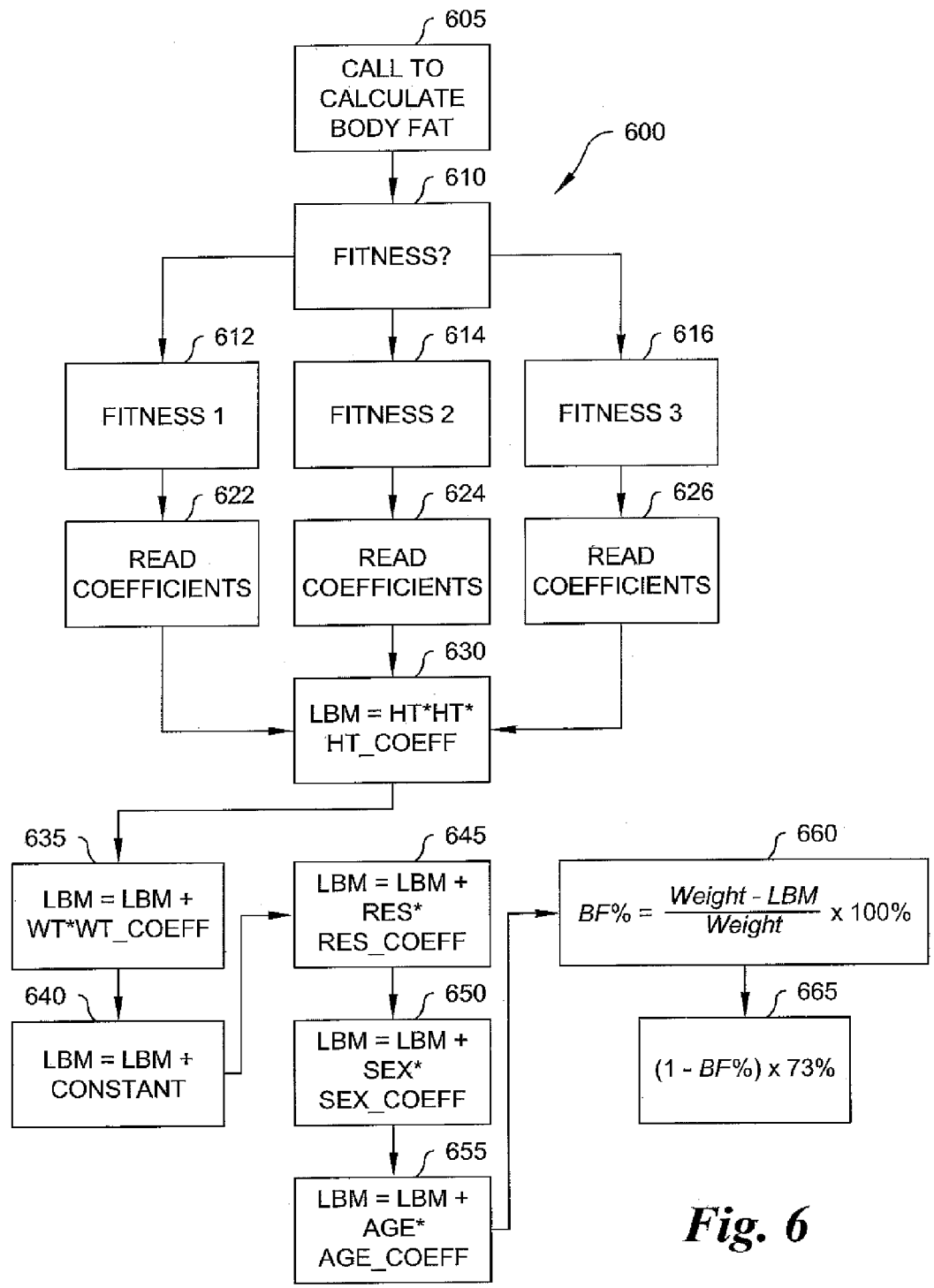
FIG. 6 is a process flow illustrating determination of body fat in accordance with the circuit and system of the present invention.

Referring now to FIG. 6, there is shown a process flow 600 for determining body fat according to an aspect of the present invention. Process flow 600 may be performed by microprocessor U1 using memory U2. Process flow 600 begins with a call to calculate body fat (process 605). Thereafter, a fitness mode is determined for the user (process 610). In the illustrated embodiment there are three fitness modes (612, 614, 616). Of course, other numbers of fitness modes may be supported. Fitness mode can generally be described in terms of exercise frequency, intensity, type. The selectable fitness modes may be used to accurately estimate body composition and % body fat for different segments of the population. Further, according to an aspect of the present invention, the various fitness modes provide a selectable and adaptive means of profile definition through the coarse of a long term, planned dievexercise program. In effect, the multiple fitness modes allow the BF % meter dynamic range to be shifted in order to better characterize the user.

In an exemplary embodiment, the first fitness mode 612 relates to a user level of activity, fitness, diet and overall personal well being characterized by a person with a relatively low level of activity. Such a person my typically limit physical activity to less than 2 times per week, with less than 20 minutes per activity at a low aerobic level. The second fitness mode 614 relates to a user level of activity, fitness, diet and overall personal well being characterized by a person who has moderate daily exercise. Such exercise may generally take the form of 20 minute workouts, 5 times per week. These types of exercise include cycling, jogging, brisk walking, raking leaves, tennis and aerobics. A person characterized as being of fitness mode 2 generally has an exercise intensity and strength at a low level as compared to a person characterized by fitness mode 3. The third fitness mode 616 relates to a user level of activity, fitness, diet and overall personal well being characterized by a person who exercises at least five times a week. Such a person regularly engages is a warm-up that includes 5-10 minutes of exercise such as walking, slow jogging, knee lifts, arm circles or trunk rotations. Low intensity movements that simulate movements to be used in the activity can also be included in the warm-up. Such a person may typically engage in a minimum of two 20-minute sessions per week that include exercises for major muscle groups, such as lifting weights. Such a person may typically engage in at least three 30-minute sessions each week that include exercises such as calisthenics, push-ups, sit-ups and pull-ups. Such a person may typically engage in at least three 20-minute bouts of continuous aerobic (activity requiring oxygen) rhythmic exercise each week. Popular aerobic conditioning activities include brisk walking, jogging, swimming, cycling, rope-jumping, rowing, cross-country skiing, and some continuous action games like racquetball and handball. Such a person may typically engage in 10-12 minutes of daily stretching exercises performed slowly, without a bouncing motion. This can be included after a warm-up or during a cool-down. And, such a person may typically engage in a minimum of 5-10 minutes of slow walking, low-level exercise, combined with stretching.

Generally, a typical person may be characterized as fitness mode 1 (Normal). When a diet/exercise regime is engaged, a user may be instructed to select fitness mode 2. Finally, after 6 months of a controlled diet/exercise regime the user may be characterized as fitness mode 3. According to an aspect of the present invention, a user may select the fitness mode utilized based upon his/her profile of activity. Alternatively, the user may be prompted with questions indicative of the aforementioned considerations, and the answers used to determine an appropriate fitness mode. Alternatively, a fitness mode can be determined using measured values and user entered values (e.g. height, sex, age, exercise frequency/type/intensity, weight, and resistance).

Referring still to FIG. 6, process 600 continues with coefficients corresponding to the selected fitness mode (process 610) being determined (process 622, 624, 626). The coefficients may be recovered from a look-up table being stored in a memory internal, or external, to the microprocessor, for example. Table-1 summarizes non-limiting, exemplary coefficient values that may be recovered 622, 624 and 626.

TABLE 1

| Coefficient | Fitness Mode 1 | Fitness Mode 2 | Fitness Mode 3 |
|---|---|---|---|
| Constant | 4.032 | 6.039 | 10.05 |
| Sex | 6.311 | 8.5 | 12.89 |
| Age | 0.0442 | 0.019 | 0.01 |
| Height | 0.000906 | 0.000912 | 0.000925 |
| Weight | 0.39 | 0.39 | 0.39 |
| Resistance | 0.0009 | 0.00083 | 0.00069 |

Referring still to FIG. 6, an iterative calculation of lean body mass (LBM) may then be used (processes 630-655). More particularly, the LBM may be approximated by first squaring a user entered height and multiplying the result by the height coefficient for the determined fitness level (process 630). The resultant value may then be added to the value of the measured weight multiplied by the weight coefficient for the determined fitness level (process 635). The resultant may then be added to the constant for the determined fitness level (process 640). The resultant value (that was stored in process 760 of FIG. 7) may then be added to the value of the measured resistance multiplied by the resistance coefficient for the determined fitness level (process 645). The resultant value may then be added to the value of the user entered sex (0 for a female and 1 for a male) multiplied by the sex coefficient for the determined fitness level (process 650). Finally, the resultant value may then be added to the value of the user entered age multiplied by the age coefficient for the determined fitness level (process 655) to produce an approximation of the LBM.

Referring still to FIG. 6, the LBM may then be used to approximate the user's percent body fat (BF %) using the equation:

$$BF\% = \frac{\text{Weight} - LBM}{\text{Weight}} \times 100\%$$

(process 660). Finally the percentage of body water (BW) may be approximated using the equation: (1−BF %)×73% (process 665).

Alternatively, processing based on age, weight, sex and resistance alone may be used, analogous to that disclosed by U.S. Pat. No. 6,292,690, the entire disclosure of which is hereby incorporated by reference herein.

Those of ordinary skill in the art may recognize that many modifications and variations of the present invention may be implemented without departing from the spirit or scope of the invention. Thus, it is intended that the present invention covers the modifications and variations of this invention provided they come within the scope of the appended claims and their equivalents.

What is claimed is:

1. An apparatus for determining body impedance comprising:
   first and second electrodes adapted for being electrically coupled to a body;
   a variable frequency relaxation oscillator circuit electrically coupled to said electrodes; and
   at least one resistor coupled across said electrodes, said at least one resistor coupled in parallel with the body,
   wherein, the period of oscillation of said variable frequency relaxation oscillator circuit is indicative of the body impedance,
   wherein the oscillator circuit comprises at least one amplifier, and
   wherein the electrodes at least partially define a negative feedback network for said amplifier.

2. The apparatus of claim 1, wherein the first of said electrodes is resistively coupled to an output terminal of said amplifier.

3. The apparatus of claim 2, wherein the second of said electrodes is coupled to common through at least one capacitor and is shorted to an inverting input terminal of said amplifier.

4. The apparatus of claim 3, further comprising a positive feedback network comprising a resistor electrically coupled between said amplifier output terminal and a non-inverting input terminal of said amplifier.

5. The apparatus of claim 4, wherein when biased and coupled to the body, said at least one capacitor charges and discharges exponentially through said electrodes with respect to said amplifier non-inverting input terminal.

6. The apparatus of claim 1, wherein said at least one resistor is at least two hundred kilo-ohms.

7. A method for measuring an impedance of a body, comprising:
   electrically coupling first and second electrodes to the body;
   electrically coupling at least one resistor across said first and second electrodes, said at least one resistor coupled in parallel with the body;
   electrically biasing a variable frequency relaxation oscillator having both a negative feedback network comprising said electrodes, and a positive resistive feedback network; and
   measuring the period of oscillation of said variable frequency oscillator, wherein the measured period of oscillation is indicative of the impedance of the body.

8. The method of claim 7, wherein the measured period of oscillation is proportional to the impedance of the body.

9. The method of claim 7, wherein the oscillator comprises at least one operational amplifier.

10. The method of claim 9, wherein the first of said electrodes is resistively coupled to an output terminal of said operational amplifier.

11. The method of claim 10, wherein the second of said electrodes is coupled to common through at least one capacitor and is shorted to an inverting input terminal of said operational amplifier.

12. The method of claim 11, wherein said at least one capacitor charges and discharges exponentially through said electrodes with respect to an operational amplifier non-inverting input terminal.

* * * * *